United States Patent
North et al.

(10) Patent No.: US 9,962,676 B2
(45) Date of Patent: May 8, 2018

(54) PROCESSING MICROTITRE PLATES FOR COVALENT IMMOBILIZATION CHEMISTRIES

(71) Applicants: Stella H. North, Alexandria, VA (US); Evgeniya H. Lock, Alexandria, VA (US); Scott G. Walton, Fairfax, VA (US); Chris Rowe Taitt, White Plains, MD (US)

(72) Inventors: Stella H. North, Alexandria, VA (US); Evgeniya H. Lock, Alexandria, VA (US); Scott G. Walton, Fairfax, VA (US); Chris Rowe Taitt, White Plains, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days. days.

(21) Appl. No.: 14/674,183

(22) Filed: Mar. 31, 2015

(65) Prior Publication Data

US 2016/0228840 A1  Aug. 11, 2016

Related U.S. Application Data

(62) Division of application No. 14/175,182, filed on Feb. 7, 2014, now Pat. No. 9,182,392, which is a division
(Continued)

(51) Int. Cl.
*B01L 3/00* (2006.01)
*G01N 31/16* (2006.01)
(Continued)

(52) U.S. Cl.
CPC .......... *B01J 19/0046* (2013.01); *B29C 59/14* (2013.01); *C08J 7/123* (2013.01); *C08J 7/16* (2013.01);
(Continued)

(58) Field of Classification Search
CPC .... B01L 3/00; G01N 31/16; C08J 7/04; C08F 8/06; C08F 8/30
(Continued)

(56) References Cited

U.S. PATENT DOCUMENTS 5,132,108 A * 7/1992 Narayanan et al. ....... 424/78.17
5,340,451 A * 8/1994 Buchwalter et al. ......... 204/165
(Continued)

OTHER PUBLICATIONS

Lock et al., "Physio-Chemical Modifications of Polystyrene and Poly(propylene) Surfaces by Electron Beam-Generated Plasmas Produced in Argon" Plasma Process. Polym. 2009, 6, 234-245 (Apr. 3, 2009).

*Primary Examiner* — Brian J. Sines
(74) *Attorney, Agent, or Firm* — US Naval Research Laboratory; Joseph T. Grunkemeyer

(57) ABSTRACT

Disclosed herein is a method of: treating an organic polymer with an electron beam-generated plasma; exposing the treated polymer to air or an oxygen- and hydrogen-containing gas, generating hydroxyl groups on the surface of the polymer; reacting the surface with an organosilane compound having a chloro, fluoro, or alkoxy group and a functional or reactive group that is less reactive with the surface than the chloro, fluoro, or alkoxy group; and covalently immobilizing a biomolecule to the functional or reactive group or a reaction product thereof.

2 Claims, 9 Drawing Sheets

Related U.S. Application Data of application No. 12/948,114, filed on Nov. 17, 2010, now Pat. No. 8,651,158.

(60) Provisional application No. 61/261,843, filed on Nov. 17, 2009.

(51) Int. Cl.

| | | |
|---|---|---|
| *B01J 19/00* | (2006.01) | |
| *B29C 59/14* | (2006.01) | |
| *C08J 7/12* | (2006.01) | |
| *C08J 7/16* | (2006.01) | |
| *G01N 33/543* | (2006.01) | |

(52) U.S. Cl.
CPC .......... *G01N 33/54353* (2013.01); *B01J 2219/00587* (2013.01); *B01J 2219/00596* (2013.01); *B01J 2219/00711* (2013.01); *B01J 2219/00725* (2013.01); *C08J 2325/06* (2013.01)

(58) Field of Classification Search
USPC .................................. 422/502, 503, 551, 552
See application file for complete search history.

(56) References Cited

U.S. PATENT DOCUMENTS

| | | | | |
|---|---|---|---|---|
| 5,344,701 | A | * | 9/1994 | Gagnon et al. ............ 428/304.4 |
| 5,576,072 | A | * | 11/1996 | Hostettler et al. ............ 427/532 |
| 5,639,308 | A | * | 6/1997 | Yamazaki ............... H01J 27/18 118/715 |
| 5,702,772 | A | * | 12/1997 | Skelly et al. .................. 427/536 |
| 5,874,807 | A | * | 2/1999 | Neger ............... H01J 37/32009 315/111.41 |
| 5,916,674 | A | * | 6/1999 | Skelly et al. .................. 428/336 |
| 5,922,470 | A | * | 7/1999 | Bracken et al. ............... 428/447 |
| 6,022,902 | A | * | 2/2000 | Koontz ........................... 521/53 |
| 2003/0130112 | A1 | * | 7/2003 | Davies et al. ................. 502/159 |
| 2004/0077075 | A1 | * | 4/2004 | Jensen et al. ............... 435/297.2 |
| 2005/0053642 | A1 | * | 3/2005 | Ulbricht et al. ............... 424/443 |
| 2005/0067099 | A1 | * | 3/2005 | Walton .................... H01J 3/025 156/345.4 |
| 2005/0112292 | A1 | * | 5/2005 | Parker et al. .................. 427/508 |
| 2005/0230242 | A1 | * | 10/2005 | Leonhardt ............. C23C 14/205 204/192.11 |
| 2006/0208649 | A1 | * | 9/2006 | Rueger ............. H01J 37/32366 315/111.21 |
| 2008/0067430 | A1 | * | 3/2008 | Hershkowitz ......... F03H 1/0025 250/492.3 |
| 2009/0181411 | A1 | * | 7/2009 | Battrell et al. ................ 435/7.92 |
| 2010/0028238 | A1 | * | 2/2010 | Maschwitz ........... C23C 16/402 423/335 |

* cited by examiner

PROCESSING MICROTITRE PLATES FOR COVALENT IMMOBILIZATION CHEMISTRIES

This application is a divisional application of U.S. Pat. No. 9,182,392, issued on Nov. 10, 2015, which is a divisional application of U.S. Pat. No. 8,651,158 issued on Feb. 18, 2014, which claims the benefit of U.S. Provisional Application No. 61/261,843, filed on Nov. 17, 2009. The provisional application and all other publications and patent documents referred to throughout this nonprovisional application are incorporated herein by reference.

TECHNICAL FIELD

The present disclosure is generally related to microtitre plates for assays.

DESCRIPTION OF RELATED ART

Microtitre plates are effective solid-phase platforms for multiplexed, high-throughput screening and analysis of biomolecule interactions. This multi-well format, available in 6, 24, 96, 384, 1536, and even 3456 or 9600-well plates, is widely used in both industry and medical fields due to its ease of automation, high capacity for paralleled data collection, and versatile application of technologies (e.g., proteomics, functional genomics, biomolecule separation and purification). Microtitre plates are manufactured using a variety of polymeric materials (e.g., polypropylene, polycarbonate), but polystyrene is most commonly employed because it readily adsorbs (via non-covalent interaction) proteins, has excellent optical as well as mechanical properties, and is cost-effective. However, several of these intrinsic properties of polystyrene also present disadvantages: poor chemical resistance, difficulty controlling surface chemistry, protein denaturation, desorption and/or loss of biomolecule activity (Rebeski et al., "Identification of unacceptable background caused by non-specific protein adsorption to the plastic surface of 96-well immunoassay plates using a standardized enzyme-linked immunosorbent assay procedure" *J. Immunological Methods*, 226, 85-92 (1999). Indeed, it has been estimated that less than 10% of adsorbed protein molecules retain their activity (Butler, "Solid Supports in Enzyme-Linked Immunosorbent Assay and Other Solid-Phase Immunoassays" *Methods*, 22(1), 4-23 (2000)).

As a consequence of the structural complexity and diversity of biological molecules and the highly specific recognition mechanism for biomolecule capture, surface attachment design must take into consideration native conformation, molecular orientation, and cross-reactivity (Kusnezow et al., "Solid supports for microarray immunoassays" *Journal of Molecular Recognition*, 16(4), 165-176 (2003)). Although the simplest means of biomolecule immobilization is through surface adsorption, a non-covalent binding event that takes place on most microtitre plates, covalent attachment schemes represent a more robust approach that can ensure functional display of the biomolecule of interest (Goddard et al., "Polymer surface modification for the attachment of bioactive compounds" *Progress in Polymer Science*, 32(7), 698-725 (2007)). Different surface modification strategies have previously been reported for the covalent attachment of biomolecules to polymeric substrates (e.g., poly(methyl methacrylate) (PMMA), polydimethysiloxane (PDMS), polystyrene (PS), polyvinylidenedifluoride (PVDF), etc.). But generally, these studies relied on variable thickness coatings of amine-bearing copolymers and biopolymers (Bai et al., "Surface Modification for Enhancing Antibody Binding on Polymer-Based Microfluidic Device for Enzyme-Linked Immunosorbent Assay" *Langmuir*, 22(22), 9458-9467 (2006); Boulares-Pender et al., "Surface-functionalization of plasma-treated polystyrene by hyperbranched polymers and use in biological applications" *Journal of Applied Polymer Science*, 112(5), 2701-2709 (2009)), inert proteins (Eteshola et al., "Development and characterization of an ELISA assay in PDMS microfluidic channels" *Sensors and Actuators B: Chemical*, 72(2), 129-133 (2001)), metals (Darain et al., "On-chip detection of myoglobin based on fluorescence" *Biosensors and Bioelectronics*, 24(6), 1744-1750 (2009)) or sol-gel matrices (Wang et al., "Microfluidic immunosensor based on stable antibody-patterned surface in PMMA microchip" *Electrochemistry Communications*, 10(3), 447-450 (2008)) applied through physical or chemical vapor deposition for covalent bioimmobilization. Ideally, surface modification approaches should aim to introduce no more than a single monolayer of a desired functional group to a substrate surface, yet in these cases, bioimmobilization has little to do with the core substrate but rather the deposited film or coating. The challenge of polymer surface engineering is underscored by the limited number of commercially available polymeric substrates (e.g., microtitre plates) that possess the correct surface characteristics to facilitate a direct, covalent biomolecule attachment.

In recent years, there has been an emerging interest in the application of self-assembled monolayers for bioimmobilization on solid support. Silane coupling chemistry is highly selective and allows the functionalization of a substrate surface with different functional groups (e.g., epoxy, amine, thiol, aldehyde, etc.). Organosilanes have been used to covalently attach biological molecules onto inorganic substrates such as silica (e.g., glass, silicon via siloxy linkage) and metal (e.g., gold, copper, silver via thiol linkage) (Plueddemann, Ed., *Silane coupling agents*. New York, Plenum Press (1991); Mittal, Ed., *Silanes and other coupling agents*. The Netherlands, VSP BV (2000)). There has been significantly less research on surface modification using silane monolayers on polymers. Polymer surface modification techniques (e.g., ion beam treatment, plasma treatment, UV/ozone treatment) have been reported to create pendant surface hydroxyl groups on polymeric surfaces, which allows the application of the same silanization chemistry used for inorganic substrates (Inagaki et al., "Surface Modification of PET Films by Pulsed Argon Plasma" *J. Appl. Polym. Sci.*, 85, 2845-2852 (2002); Kawase et al. "End-capped fluoroalkyl-functional silanes. Part II: Modification of polymers and possibility of multifunctional silanes" *Journal of Adhesion Science and Technology*, 16, 1121-1140 (2002); Cheng et al., "Direct-write laser micromachining and universal surface modification of PMMA for device development" *Sensors and Actuators B: Chemical*, 99(1), 186-196 (2004); Prissanaroon et al., "Fabrication of patterned polypyrrole on fluoropolymers for pH sensing applications" *Synthetic Metals*, 54, 105-108 (2005); Long et al., "Water-Vapor Plasma-Based Surface Activation for Trichlorosilane Modification of PMMA" *Langmuir*, 22, 4104-4109 (2006)). However, in these previous studies, the organosilanes lacked reactive end-functionalities and were deposited on the polymeric surface primarily as a means of modulating surface properties (e.g., adhesion, wettability). Polystyrene can be chemically treated to support silane-dependant attachment of biomolecules in enzyme-linked immunosorbent assay (Kaur et al., "Strategies for direct attachment of hapten to a polystyrene support for applications in enzyme-linked immunosorbent assay (ELISA)", *Analytica Chimica Acta,* 506(2), 133-135 (2004)), but as with most wet methods for surface modification, this approach requires extensive treatment in corrosive solutions that result in the non-specific biomolecule attachment, irregular surface etching and the production of a wide range of oxygen containing functional groups (e.g., C=O, O—C=O, $CO_3$) and therefore less useful for applications that require more specific functionalities.

In addition to the surface attachment mechanism, three-dimensional surface structures, as those created by chemical and physical etching techniques or thin film deposition, also play a significant role in modulating efficacy of bioimmobilization and functionality of the biointerface. Surface morphology has been shown to affect the activity of the immobilized biomolecule, specific and non-specific binding of macromolecules and cells, as well as surface energy of the core substrate (Cretich et al., "A new polymeric coating for protein microarrays" *Analytical Biochemistry,* 332(1), 67-74 (2004); Chiari et al., "Peptide microarrays for the characterization of antigenic regions of human chromogranin A" *Proteomics,* 5(14), 3600-3603 (2005); Tuttle et al., "Influence of biologically inspired nanometer surface roughness on antigen-antibody interactions for immunoassay-biosensor applications" *Int. J. Nanomedicine,* 1(4), 497-505 (2006)). Surface roughness can significantly alter the biophysical and biochemical behavior of the biointerface (Lamb et al., "Enzyme immobilisation on colloidal liquid aphrons (CLAs): the influence of protein properties" *Enzyme and Microbial Technology,* 24(8-9), 541-548 (1999); Wentworth et al., "Application of chitosan-entrapped beta-galactosidase in a packed-bed reactor system" *Journal of Applied Polymer Science,* 91(2), 1294-1299 (2004)). When surface roughness and surface chemistry are both altered, as it is typically the case for most surface modification methods, it is difficult to identify the contribution of each variable to specific and non-specific biomolecule attachment and activity. Therefore, advanced surface engineering is necessary to provide precise, independent control of chemical functionality (i.e., density and type of reactive moieties) and surface topology (i.e., surface roughness) down to the nanometer scale.

BRIEF SUMMARY

Disclosed herein is a method comprising: treating an organic polymer with an electron beam-generated plasma; exposing the treated polymer to air or an oxygen- and hydrogen-containing gas; reacting the surface with an organosilane compound having a chloro, fluoro, or alkoxy group and a functional or reactive group that is less reactive with the surface than the chloro, fluoro, or alkoxy group; and covalently immobilizing a biomolecule to the functional or reactive group or a reaction product thereof. The treating and exposing generates hydroxyl groups on the surface of the polymer.

Also disclosed herein is an article comprising: a polymeric microtitre plate comprising a plurality of wells and two or more different organosilane compounds having a functional or reactive group and bound to the surfaces of the wells. At least two of the wells have different organosilane compounds bound therein Also disclosed herein is an article comprising: a polymeric microtitre plate comprising a plurality of wells and one or more organosilane compounds bound to the surfaces of the wells. The organosilane compounds in at least two different wells are each reacted with a different crosslinker.

Also disclosed herein is a method comprising: treating an organic polymer microtitre plate with an electron beam-generated plasma; and exposing the treated polymer to air or an oxygen- and hydrogen-containing gas. The treating and exposing generates hydroxyl groups on the surface

BRIEF DESCRIPTION OF THE DRAWINGS

A more complete appreciation of the invention will be readily obtained by reference to the following Description of the Example Embodiments and the accompanying drawings.

FIG. 2A shows a plasma-treated plate incubated with MPTES. FIG. 2B shows a non-plasma-treated plate incubated with MPTES. FIG. 2C shows a plasma-treated plate incubated with APTES. FIG. 2D shows a non-plasma-treated plate incubated with APTES. Microfluor I (NUNC) polystyrene microtitre plates were treated using sample C7 conditions (Table 3). Plasma-treated plates (A and C) and non-plasma-treated plates (B and D) were then incubated with thiol- or amine-terminated silanes (specifically, 3-mercaptopropyl (MPTES) (A and B) and 3-aminopropyl tri(m)ethoxy silanes (APTES) (C and D)) followed by incubation with a thiol specific GMBS or amine specific BS3 crosslinker. The plates were rinsed with water and solutions containing fluorescently-labeled antibodies were added to wells. Plates were further incubated in PBS containing 0.05% Tween-20 to remove adsorbed proteins and measured for bound fluorescence, indicating the covalent attachment of fluorescent protein. Multiple controls were included: ±plasma treatment, ±APTES and MPTES, ±GMBS and BS3, and different concentrations of fluorescent protein.

DETAILED DESCRIPTION OF EXAMPLE EMBODIMENTS

Figure 1:
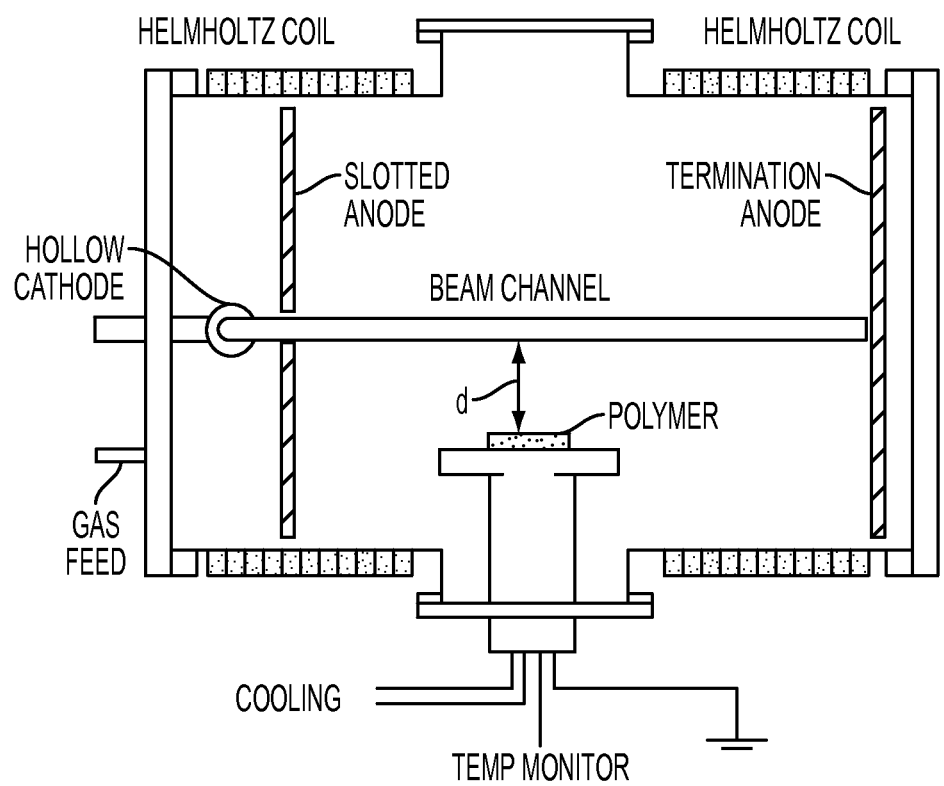
FIG. 1 schematically illustrates an example plasma-generating apparatus.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Microtitre plates are now a standard tool in analytical research and clinical diagnostic testing laboratories, most specifically for enzyme-linked immunosorbent assays (ELISAs). The most commonly used material for the production of microtitre plates is polystyrene, due to its clarity when used unadulterated and its propensity to adsorb biomolecules of interest, such as antibodies and other proteins. Although attachment through adsorption is simple and easy, biomolecules immobilized in this way may desorb under a variety of conditions, and their activity and/or presentation may be compromised by the random orientation by which they are adsorbed. Additionally, many biomolecules cannot be reproducibly immobilized in functional form on standard polystyrene microtitre plates. For this reason, microplates capable of covalent attachment of biomolecules have been developed and are now commercially available. These include maleic anhydride- and maleimide-activated microplates (Thermo Scientific) and Immobilizer Amino plates (Nunc). Although useful in many settings, these plates are significantly more expensive than standard, untreated polystyrene. Furthermore, these plates require that a single (pre-defined) attachment chemistry be used in all wells, limiting the types of biomolecules that can be immobilized, as well as their orientations.

The present method may be used to produce chemically functionalized microtitre plates that can allow multiple covalent immobilization chemistries to be performed on a single plate for bioassay applications. Microtitre plates processed using this methodology may have versatile and predictable functionality and may possess surface properties that enable the user to tailor the immobilization chemistry to suit the biomolecule of interest.

Plasma treatments are a fine-tunable, dry alternative to commonly used wet methods for the modification of polymeric surfaces (Davies et al., "Argon plasma treatment of polystyrene microtiter wells. Chemical and physical characterisation by contact angle, ToF-SIMS, XPS and STM" *Colloids and Surfaces A: Physicochemical and Engineering Aspects,* 174, 287-295 (2000); Weikart et al., "Modification, Degradation, and Stability of Polymeric Surfaces Treated with Reactive Plasmas" *J. Polym. Sci. Part A: Polym. Chem.,* 38, 3028-3042 (2000); Guruvenket et al., "Plasma surface modification of polystyrene and polyethylene" *Applied Surface Science,* 236, 278-284 (2004)). Plasma treatment reduces the generation of hazardous chemical wastes with less degradation and roughening of the material than wet chemical treatments. The advantage of plasma-based surface engineering is derived from the delivery of energetic ions and unique reactive species, which produces chemical moieties at the surface. Complex surface chemistries can be attained by simply varying the gas that is used (e.g., Ar, $N_2$, $O_2$, $H_2O$, $CO_2$, $NH_3$), which provides the opportunity to endow the surface with specific and non-specific performance features (Lane et al., "Surface treatments of polyolefins" *Progress in Organic Coatings,* 21(4), 269-284 (1993). Indeed, plasmas have been used to improve wettability, hydrophobicity, and biocompatibility of a wide variety of polymers (Garrison et al., "Glow discharge plasma deposited hexafluoropropylene films: surface chemistry and interfacial materials properties" *Thin Solid Films,* 352(1-2), 13-21 (1999); Grace et al., "Plasma Treatment of Polymers" *Journal of Dispersion Science and Technology,* 24(3), 305-341 (2003); Hegemann et al., "Plasma treatment of polymers for surface and adhesion improvement" *Nuclear Instruments and Methods in Physics Research Section B: Beam Interactions with Materials and Atoms Ionizing Radiation and Polymers,* 208, 281-286 (2003); Lopez et al., "Immobilization of RGD peptides on stable plasma-deposited acrylic acid coatings for biomedical devices" *Surface and Coatings Technology PSE* 2004, 200(1-4), 1000-1004 (2005)).

Although energetic ions promote the various surface chemistries that are desired, they can also be problematic. Consider that ions produced in conventional plasma discharges will impact the surface with energies on the order of 10-50 eV, which exceeds the binding energies of polymeric materials and can produce excessive surface roughening and etching and promote the incorporation of non-native elements well below the surface. In addition, conventional discharges produce large densities of excited species, leading to a significant flux of photons at the surface. These photons can penetrate several hundred nanometers into the surface, inducing subsurface chemical changes that may not be beneficial. The combination of these effects likely lead to the well-known ageing behavior in plasma modified polymers (Haidopoulos et al., "Angle-Resolved XPS Study of Plasma-Deposited Polystyrene Films after Oxygen Plasma Treatment" *Plasma processes and polymers,* 5(1), 67-75 (2008)), which could lead to relaxation to pre-treatment conditions.

In the disclosed method, an electron beam generated plasma is used, with the ability to selectively alter the top few nanometers of a material's surface without changing the bulk properties, generating reactive chemical moieties that are incorporated at, rather than deposited on, the surface of a polymer. The properties of the plasmas used in this method include the delivery of ions with energies below the binding energy of polymeric materials and a low production of photons. The electron temperature (or the average electron energy) determines the production species and also the energy of ions incident to adjacent surfaces. In conventional discharges, plasma electrons are energized via the application of electric fields, producing a distribution of electron energies with an average energy in the range of 2-10 eV. Only a small fraction of the electrons are energetic enough to ionize the gas so most of the electron energy is spent to excite the gas, producing large densities of molecular fragments and excited species, which decay via photon emission. Moreover, the electron temperature determines the plasma's potential and thus determines the energy at which ions leave the plasma. In electron beam generated plasmas, a high-energy (≈keV) electron beam is used to ionize the gas and the cross section for electron-impact ionization at keV energies can be orders of magnitude higher than the excitation cross sections. Thus, these sources generate a lower relative fraction of excited species that produce photons. The electron temperature in these plasmas is lower due to the absence of the electric fields that are used in discharges. The resulting electron temperatures are gas dependent but range between about 0.3 and 1 eV. Thus, incident ion energies are at or near the bond strength of most polymeric materials. These characteristics result in low etch rates, small changes in surface morphology, and generally induces chemical modifications limited to the top few nanometers of the polymer surface.

The method described herein consists of three steps that employ both dry and wet chemical processing of microtitre plates to yield a customized, multi-site covalent bioimmobilization platform for biomedical and biological applications. The method combines the electron beam plasma source described above to introduce surface hydroxyl (OH) with secondary surface modification step using reactive end functionalized organosilanes. Multifunctional silane coupling agents combined with covalent crosslinkers of various functionalities and spacer lengths ensures the stable attachment and functionally active biological compounds. The three steps can be used in tandem to create microtitre plates with versatile and predictable functionalities that enable the user to tailor the immobilization chemistry to suit the biomolecule of interest. Each step is described in detail in the following sections.

In the first step, an electron beam generated plasma is used to introduce pendant hydroxyl groups onto the surface of an organic polymer. The plasma generating apparatus may be that disclosed in Meger et al., U.S. Pat. No. 5,874,807. FIG. 1 schematically illustrates an example plasma-generating apparatus. This apparatus uses a linear hollow cathode to produce a sheet-like electron beam. The shape of the beam can be maintained by a magnetic field. One typical set of beam dimension is length of 50 cm, width of 25 cm, and thickness of 1 cm.

Organic polymers may have a carbon-based backbone. Any organic polymer may be used including polystyrene microtitre wells or a polymer, such as polystyrene or polyethylene, spin-coated onto a substrate. This plasma differs notably from discharge plasmas, which are created by applying electric fields to a gas volume. In electron beam generated plasma, a high energy electron beam is injected into the gas, which ionizes, dissociates, and excites the gas. The resulting plasma differs from discharge plasmas in species generation and spatial evolution. Moreover, the inherently lower electron temperature results in a lower plasma potential and thus the kinetic energy of ions impacting adjacent surfaces is lower. Suitable gases for generating the plasma include, but are not limited to, argon, oxygen, carbon dioxide, dry air, humid air, a gas with water vapor, or a mixture thereof. The treated polymer is then exposed to air or other gas containing oxygen and hydrogen. Depending on the gasses used, the hydroxyl groups may be generated by either the plasma treatment or the exposure to air.

When the plasma gas is argon, one set of suitable operating conditions are within +/−10% of: gas pressure of 90 mTorr, treatment time of 2 minutes, electron beam energy of 2 keV, electron beam current density of 4 mA/cm$^2$, electron beam pulse width of 2 ms, electron beam pulse frequency of 50 Hz. Other suitable conditions using different gases are described by Lock et al. "Surface Composition, Chemistry, and Structure of Polystyrene Modified by Electron-Beam-Generated Plasma" *Langmuir*, 26, 8857-8868 (2010). Generally, increasing the treatment time or gas pressure increases the total ion flux to the surface, which can increase the concentration of hydroxyl groups on the surface. However, an excessive ion flux may cause an increase in etching and favor chain scission over crosslinking as the dominant mechanism, reducing the yield of hydroxyl groups. Example 2 shows the results of such variance.

Figures 2A, 2B:
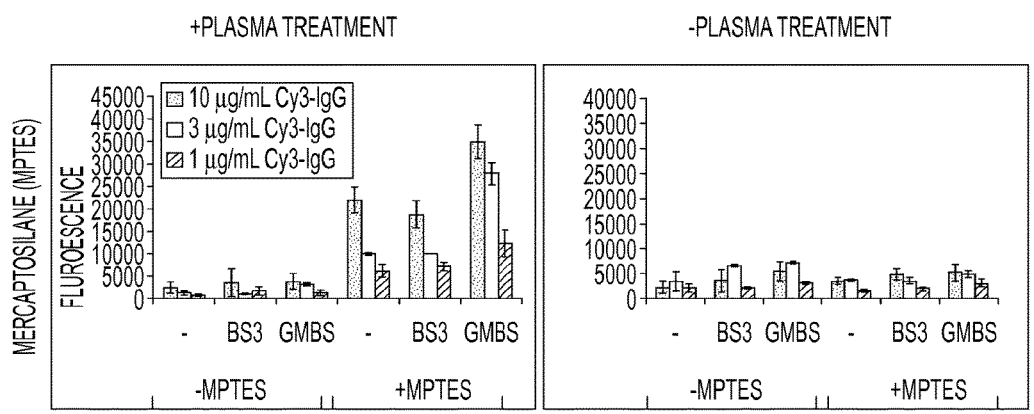
FIGS. 2A-D show bioimmobilization assays.
Figures 2C, 2D:
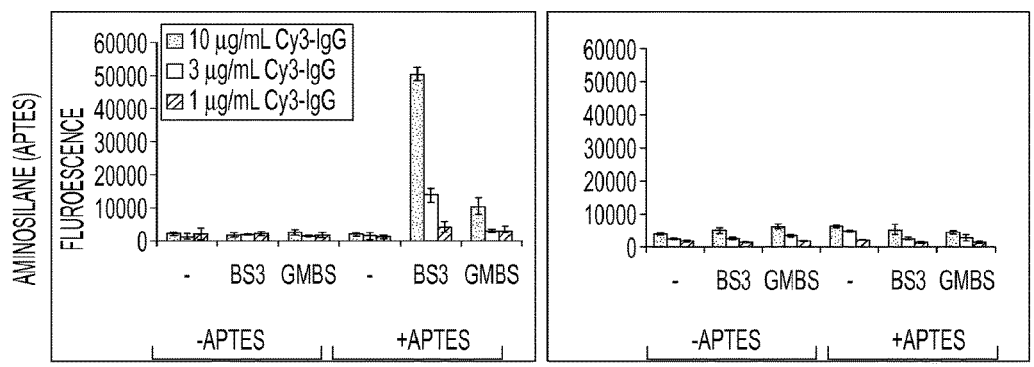

For the second step in the process, plasma-treated microtitre plates displaying the necessary pendant surface hydroxyls are covalently modified with an organosilane coupling agent possessing a functional or reactive group at one end and one or several alkoxy or chloro groups at the other. Suitable general organosilane formulas are R—SiX$_3$ and R'—(CH$_2$)$_n$—SiX$_3$. R and R' contain the functional or reactive group. Each X is an independently selected chemical group with the proviso that at least one X is chloro, fluoro, bromo, halo, or alkoxy group. The value n is a positive integer, including but not limited to integers from 1 to 25. Covalent attachment of the organosilane to the plasma-treated microplate surface yields a functionalized surface with pendant functional or reactive group capable of being used in a subsequent covalent coupling reaction. Given the large number of possible linking covalent methodologies used in subsequent steps, any organosilane terminating in any of the following functional or reactive groups (R or R') can be potentially used:

Functional groups:
  Amine—can be coupled to amines, thiols, carboxyls
  Thiol—can be coupled to amines, thiols, carboxyls
  Aldehyde—can be coupled to amines
  Carboxyl/nitrobenzyl-protected carboxyl groups—can be coupled to amines
Reactive groups:
  Glycidoxy (epoxy/epoxides)—can couple to thiols, hydroxyls (pH-dependent)
  Thiocyano, Isocyanate—can couple to hydroxyls, amines
  Succinimidyloxy- or succinimidyl ester—can couple to amines
  aryl azides/azido groups—non-selective linkage (photoactivatable)
  Hydrazine/hydrazide—can couple to aldehydes, oxidized carbohydrates
  Alkyl halide, benzyl halide, α-halo acetyl—can couple to sulfhydryls
  Maleimide—can couple to sulfhydryls Silanes possessing these terminal groups are commercially available, but others terminating in additional functional or reactive moieties can also be used. For the work here, thiol- and amine-terminated silanes (MPTES and APTES) were incubated with plasma-treated plates, resulting in covalent functionalization with thiol and primary amine moieties, respectively, that are further modified with thiol or amine specific crosslinkers (FIG. 2, panels A and C). The results support the suggestion that multiple chemistries may be carried out on a single plate.

More than one different organosilane compounds may be used on the same microtitre plate, using different compounds in different wells. This allows for the use of different chemistries for biomolecule attachment. The present method can result in the reproducible formation of a monolayer of the organosilane compound on the polymer surface, with the function or reactive groups primarily oriented away from the surface. This can be spatially favorable for attachment of the biomolecules. Other methods can cause a buildup of a thicker layer of the organosilane compound in random orientations. The monolayer can also result in unique activities of the biomolecules not found on other microtitre plates.

The third step in the process entails covalent attachment of biomolecules to the silane-functionalized surface, which may take place as a single step (e.g., addition of a biomolecule to a silane-functionalized surface with a reactive terminal group; addition of a pre-activated protein) or as multiple steps (e.g., addition of a crosslinker, followed by the biomolecule). Suitable biomolecules include, but are not limited to, peptides, antimicrobial peptides, carbohydrates, lipids, antibodies, and proteins. These single- or multi-step methods for covalent attachment of biomolecules to the silane functionalized surfaces may be accomplished by numerous methods, including but not limited to the following methods.

(1) Addition of bi- or tri-functional chemical crosslinkers, with simultaneous or subsequent incubation with biomolecule. A plethora of homo- and heterobifunctional crosslinkers are available commercially. These compounds will possess reactive groups on each end (e.g., maleimide, N-hydroxysuccinimidyl (NHS) ester) that are designed to form a covalent adduct with functional groups such as thiols and amines, respectively. Examples of bifunctional linkers include GMBS (maleimide/NHS ester), BS3 (NHS ester/NHS ester), PMPI (maleimide/isocyanate), sulfo-HSAB (NHS ester/[photoactivatable] phenyl azide), and EMCH (maleimide/hydrazide). Also considered included in this group of chemical crosslinkers are the carbodiimides; this category of molecules mediates coupling between carboxyls and primary amines (or hydrazides), resulting in a zero-length linkage and no addition of a "spacer".

(2) Use of light to activate a terminal photoactivatable group on the covalently bound silane, with simultaneous or subsequent incubation with biomolecule. Several examples of photoactivatable silanes exist that can be activated using ultraviolet or visible light: in general, the highly reactive intermediates (e.g., nitrenes) formed upon photolysis will create covalent links non-specifically with amine, sulfhydryl, carbonyl, carboxyl, and reactive hydrogen groups. An alternate example of photo-induced modification of a silane terminal group is the uv-mediated conversion of aldehyde-terminated monolayers of triethyoxysilylundecanal to carboxy-terminated layers (Hozumi et al., "Formation of aldehyde- and carboxy-terminated self-assembled monolayers on $SiO_2$ surfaces" *Surf Interface Anal.*, 40, 408-411 (2008)); these newly-formed carboxyl moieties can then presumably be used to attach amine-containing biomolecules as described in (1) above.

(3) Use of pH or hydration to activate terminal reactive moieties present on the covalently attached silane and simultaneous or subsequent incubation with biomolecule. A number of silanes terminated in reactive groups such as maleimide, NHS-ester, and isocyanate which will, under specific conditions, react with thiols, amines, and/or hydroxyls, respectively. Epoxide-terminated silanes (e.g., (3-glycidoxypropyl)trimethoxysilane) are a special case wherein the pH of the reaction dictates the specificity of covalent bond linkage; formation of thioether links (attachment to thiols) can occur at lower pHs than secondary amine linkages (attachment to amines) or ether links (attachment to hydroxyls)

(4) Incubation with a modified biomolecules possessing a reactive group specific to the silane's terminal moiety. One example is incubation of an activated protein such as maleimide- or glutaraldehyde-activated horseradish peroxidase (obtained from Pierce) with plate coated with a thiol- or amine-terminated silane, respectively.

More than one of these crosslinking methods may be used on a single plate, with different methods used in different wells. This is the case whether the wells contain the same or different organosilane compounds.

A key feature of using this method to modify microtitre plates is that, after initial plasma treatment to create surface hydroxyls, the choice of how each biomolecule can be attached is decided by the user. More specifically, by utilizing different combinations of silanes and biomolecule-linking chemistries, the user can attach different biomolecules in discrete locations on the microplate (i.e., different wells) using an appropriate covalent attachment chemistry tailored specifically to the individual biomolecules; likewise, one biomolecule can be covalently immobilized in multiple wells using different attachment chemistries.

The coupling of both dry and wet chemical methods to yield functional surfaces may have a number of advantages. Plasma treatment produces a uniform, functionalized surface that is amenable to broad range of chemistries. The wet chemical processing steps are variable such that, a large variety of biomolecules can be immobilized. Moreover, the methods described are addressable in terms of location—an advantage not afforded by commercial activated plates which utilize a single attachment chemistry for all wells. That is, while plasma can functionalize the entire plate, different wet chemistries can be applied to different wells, allowing a wider variety of biomolecules to be immobilized, using wider variety of covalent attachment chemistries.

An additional potential advantage is the lowered cost involved in manufacturing these custom-tailored plates. Manufacture of microtitre plates used in clinical diagnostics, monitoring of foodstuffs, biotech, vaccine and therapeutics development, and many other areas of basic and applied research represents a multi-billion dollar enterprise. This method allows the user to save significant costs in tailoring the attachment chemistry to the biomolecule: standard hydrophobic microtitre plates costing ~$3 each are converted to plates capable of covalent attachment chemistry; commercial plates capable of similar covalent attachment chemistries typically cost $15 to $25 each.

The following examples are given to illustrate specific applications. These specific examples are not intended to limit the scope of the disclosure in this application.

Example 1

Materials

Microfluor I and NUNC Immobilizer Amino 96-well microtiter plates were obtained from Thermo Fisher Scientific (Rochester, N.Y.). Rabbit anti-lipid A (*Escherichia coli*) IgG was purchased from AbD Serotec (Raleigh, N.C.). Antimicrobial pep-tides (AMPs) cecropin A, cecropin P1, melittin, and cecropin A(1-8)-melittin (1-18) amide were received from American Peptide Company, Inc. (Sunnyvale, Calif.). Cy3 monofunctional N-hydroxysuccinimidyl ester, 4-maleimidobutyric acid N-hydroxysuccinimide ester (GMBS), and bis(sulfosuccinimidyl) suberate ($BS^3$) were purchased from Amersham-Pharmacia (Piscataway, N.J.). Lipopolysaccharide (LPS) from *Salmonella typhimurium*, (3-mercaptopropyl)triethoxysilane (MTPES), (3-aminopropyl)triethoxysilane (APTES), phosphate buffered saline (PBS), pH 7.4, potassium hydroxide, Tween-20, bovine serum albumin (BSA), dimethyl sulfoxide (DMSO), and methanol were purchased from Sigma-Aldrich (St. Louis, Mo.).

Preparation of Fluorescently Labeled IgG and LPS

Rabbit IgG and LPS were conjugated with Cy3 monoreactive dye following manufacturer's instructions. Briefly, one mg IgG or LPS in 50 mM sodium borate, pH 8.5 was incubated with one packet of Cy3 monoreactive dye, previously dissolved in 25 µL anhydrous DMSO. After 1 h incubation at room temperature, the labeled IgG and LPS were purified from unincorporated dye by gel filtration on BioGel P-10 and BioGel P-2, respectively (BioRad, Hercules, Calif.). The labeled biomolecules were stored in the dark at 4° C. until use. The molar ratios of dye to labeled species ranged from 1.7 to 3.5 for antibodies and 1.1 to 1.4 for LPS.

Microtitre plates were exposed to pulsed, electron beam generated plasma produced in argon, which activates the plate surface. OH groups are formed on the surface upon exposure to air, most likely resulting from dissociative adsorption of $H_2O$. The experimental apparatus is discussed at Leonhardt et al., *IEEE Trans. Plasma Sci.*, 33, 783 (2005). The system vacuum was maintained by a 250 L/s turbo pump, with a base pressure of $5 \times 10^{-6}$ Torr. The operating pressure was achieved by introducing argon (purity>99.9999%), through mass flow controllers and by throttling the pumping speed using a manual gate valve. The electron beam was produced by applying a −2 kV pulse to a linear hollow cathode for a selected pulse width and duty factor. The emergent beam passed through a slot in a grounded anode and was then terminated at a second grounded anode located further downstream. Beam spreading from collisions with the background gas was suppressed by a coaxial magnetic field (150 G) produced by a set of external coils. The microtiter plates were placed on a 10.2 cm diameter stage located at 2.5 cm from the nominal edge of the electron beam. The stage was held at ground potential and room temperature.

Microtiter Plate Silanization and Immobilization of IgG

NUNC Microfluor I 96-well microtiter plates were rinsed with methanol prior to silanization. Microwells were covered with 100 μL of 2% silane solution (MPTES or APTES) prepared in methanol adjusted to pH 4 by addition of several drops acetic acid. After 30 min of incubation under nitrogen, plates were removed, rinsed three times in methanol, and dried. Cross-linking was performed by covering microwells with 100 μL of 1.0 mM GMBS in absolute ethanol and incubating for 30 min. Alternatively, 100 μL of 50 mM $BS^3$ in 10 mM phosphate buffer, pH 6.0, was used. Plates were rinsed thrice with 200 μL deionized water and dried; 1 μg/mL, 3 μg/mL, or 10 μg/mL Cy3-labeled antibody (in PBS) was then added into each microwell and allowed to incubate for 2 h at room temperature with gentle agitation; each concentration was patterned in quadruplicate. Each microwell was washed three times with 250 μL of PBS with 0.005% Tween 20 (PBST). One-hundred microliters of PBS was added to each microwell and the plate was read on a Tecan Safire microplate reader.

Immobilization of Peptides and LPS Binding Assay

Microwells were covered with 100 μL of 2% mercaptosilane solution prepared in acidic methanol and incubated for 30 min under nitrogen. Cross-linking was accomplished by covering microwells with 100 μL of 1.0 mM GMBS in absolute ethanol and incubated for an additional 30 min. One-hundred microliters of antimicrobial peptide solution (250 μg/mL in PBS) was added to each well and allowed to incubate at room temperature for 2 h with gentle agitation; each peptide was patterned in quadruplicate. For detection, after three washes with PBST, each well received 100 μL of Cy3-conjugated LPS and was incubated for 2 h at room temperature with gentle agitation. After this time, each microwell was washed three times with PBST; 100 μL PBS was added to each microwell and the plate was read on the Tecan microplate reader. For comparison of binding patterns, peptides were also immobilized onto standard glass slides as previously described using MPTES and GMBS (Kulagina et al., *Anal. Chim. Acta*, 575, 9 (2006); Taitt et al., in *Peptide Microarrays: Methods and Protocols*; Cretich, M. Chiari, M., Eds.; Springer: New York, 2009; p 233). Cy3-labeled LPS was applied to the glass-immobilized peptides and incubated for 2 h, prior to washing with PTST and imaging using a Packard ScanArray Lite confocal microarray scanner; data were extracted from images using QuantArray microarray analysis software. To emphasize the differences in the patterns of binding, as well as to account for disparity in measurements obtained on the two instruments (microarray scanner, micro-titer plate reader), data from both microtiter plates and glass slides were normalized with respect to LPS-melittin binding.

Water Contact Angle (WCA) Measurements

Goniometry was performed using a static sessile drop technique on micro-titer plate fragments. Contact angle measurements were performed at room temperature using a goniometer (AST Products, Inc.), equipped with a microsyringe to control volume of the liquid drop (2 μL). Four water drops were placed at different locations on each substrate surface. Eight contact angle measurements (each side of one water drop) were averaged and corresponding standard deviation were calculated for each plate fragment.

X-Ray Photoelectron Spectroscopy (XPS)

Surface elemental and chemical state analyses were performed on a K-Alpha X-ray photoelectron spectrometer (Thermo Scientific). This instrument is equipped with a microfocusing monochromator (Al-Kα X-ray source, 1486.6 eV), which was operated at a spot size of 400 μm. Analyzer pass energies of 200 and 25 eV respectively were used for elemental survey and chemically sensitive narrow scan spectra. The detection angle was 0°, which provides average analyzed depth down to 10 nm. K-Alpha's charge compensation system was used during the analysis, utilizing very low energy electrons and argon ions to prevent any localized charge build-up. Spectra were referenced to the main C 1s peak at 285.0 eV and quantified using Scofield sensitivity factors. The high-resolution elemental spectra were fitted using a commercial XPS analysis software package Unifit as previously described (Lock et al., *Langmuir*, 26, 8857-8868 (2010)). Briefly, the multiple-component fitting in the C 1s region always started from the lowest binding energy component and its full width at half-maximum was allowed to vary. A convolution of Gaussian and Lorentzian line shapes was assumed for individual peaks, following the line shape parametrization. To produce consistent fits of minor C 1s components, their widths were constrained to the FMHW of the first peak and their positions were assigned as follows C—$CO_2$ 285.7 eV, C—O 286.6 eV, CdO 287.6 eV, and O—CdO 289 eV. A linear combination of Shirley and linear functions with consistent parameters was used to model the background.

Atomic Force Microscopy (AFM)

The polymer surface morphology was examined using an atomic force microscope (Nanoscope III, Veeco Metrology, Santa Barbara, Calif.) operated in tapping mode. Surface images were obtained from 5×5 μm² scans at resolution of 256×256 pixels and scan rate of 1 Hz. For a quantitative evaluation of the topography changes, root-mean-square (rms) roughness was calculated from the surface height data $z_i$ using $$R_q = \left[ \frac{1}{N} \sum_{i=1}^{N} |z_i - \bar{z}|^2 \right]^{1/2}$$

where z is the mean height.

Characterization of Polystyrene Microtiter Plates after Plasma Treatment

Figure 3A:
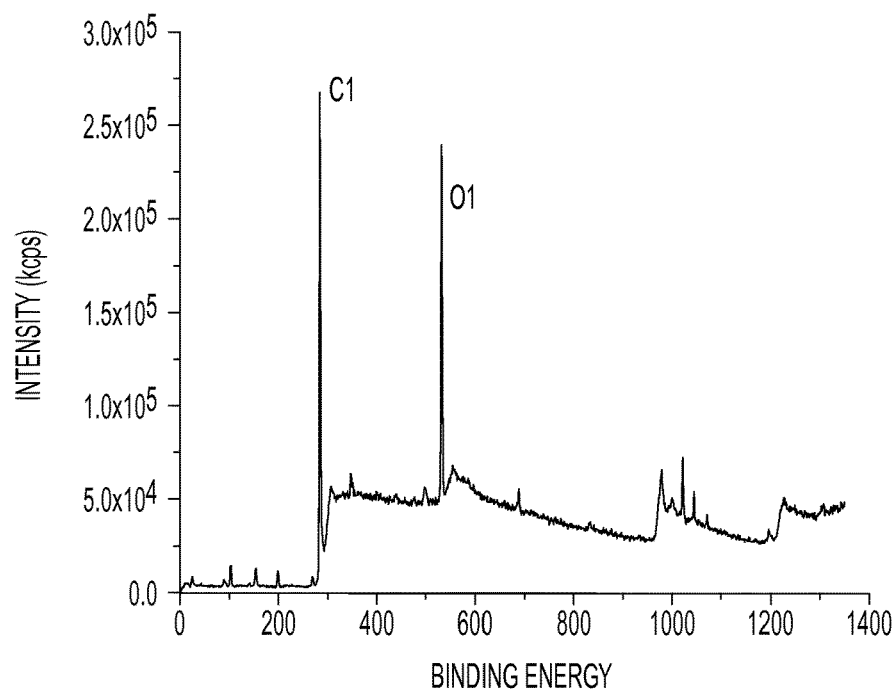
FIG. 3A shows an XPS survey spectrum of a plasma-treated microtitre plate using the optimum conditions discussed herein and FIG. 3B shows an XPS survey spectrum of an untreated microtitre plate.
Figure 3B:
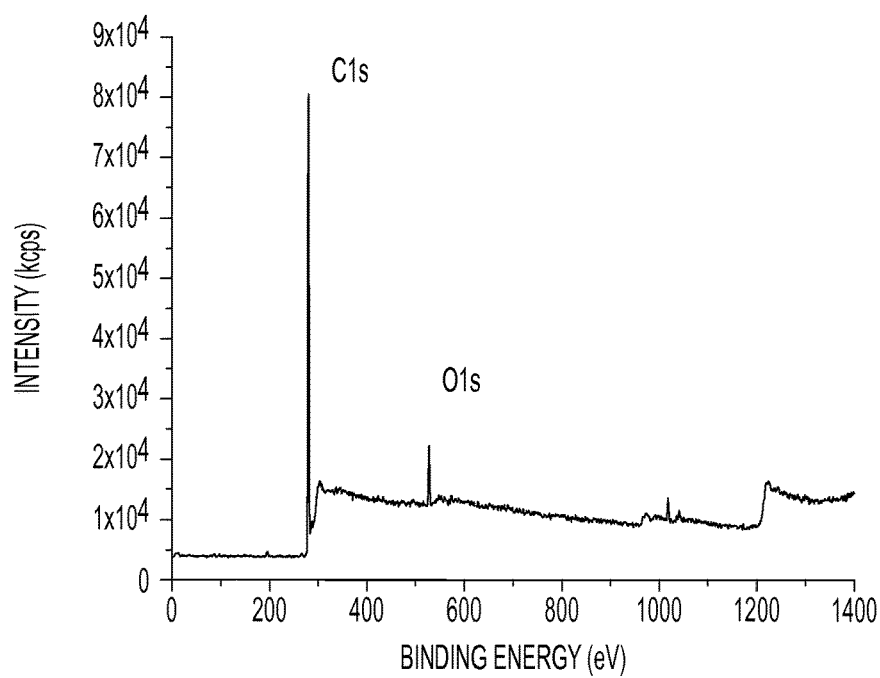
Figure 4A:
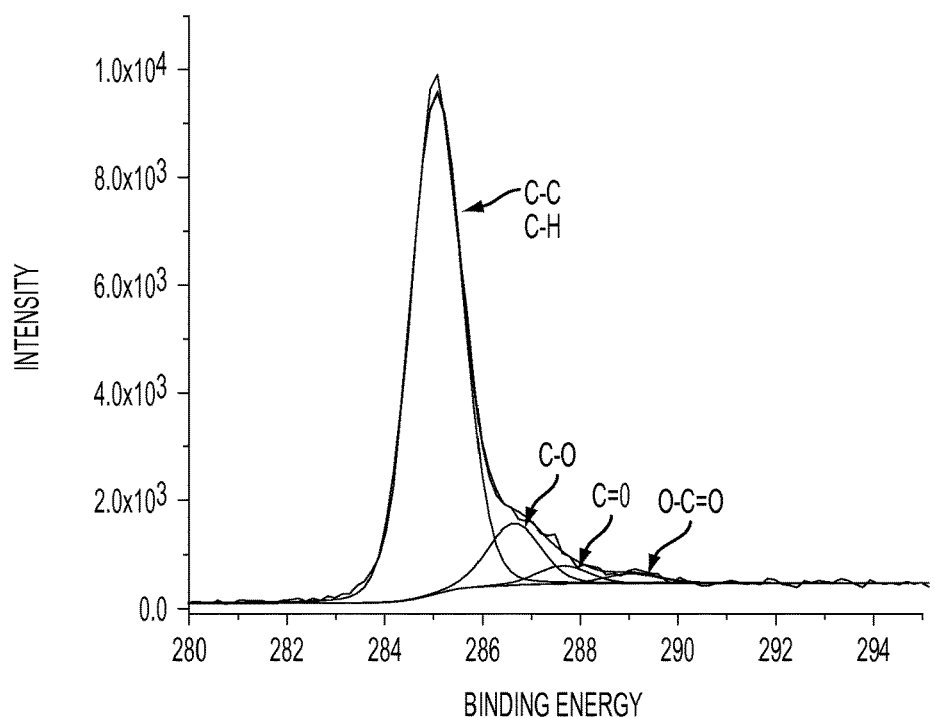
FIG. 4A shows an XPS high resolution spectrum of the C1s peak for a plasma treated microtitre plate and FIG. 4B shows an XPS high resolution spectrum of an untreated microtitre plate.
Figure 4B:
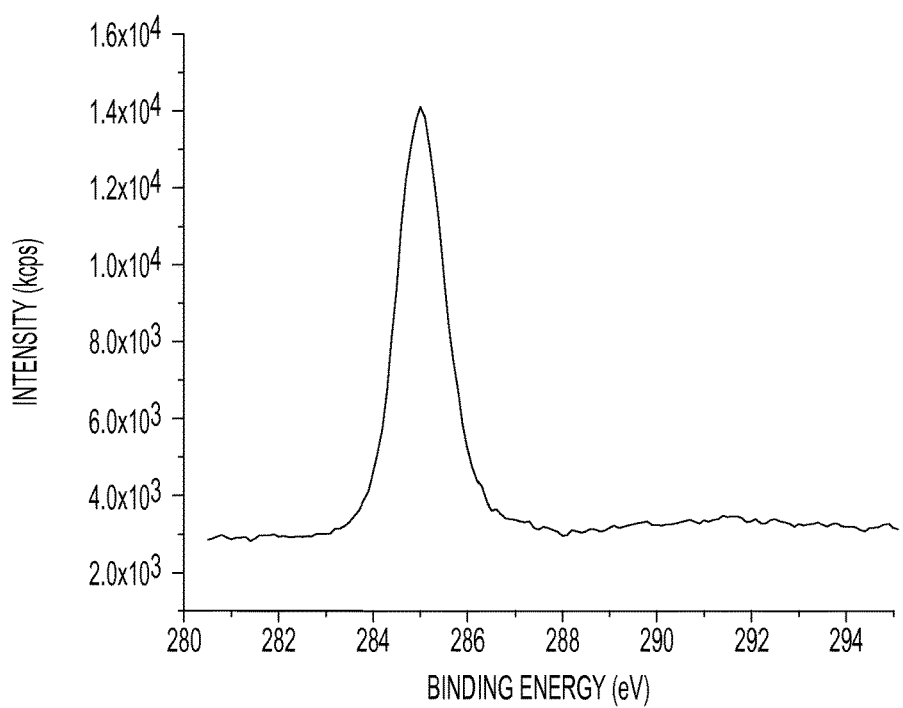
Figure 5A:
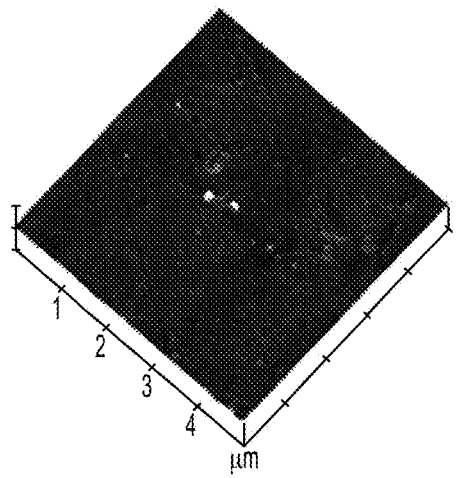
FIG. 5A shows an AFM image of an untreated microtitre plate.
Figure 5B:
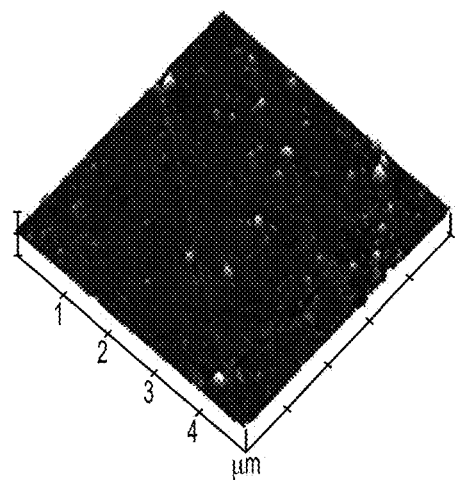
FIG. 5B shows an AFM image of an untreated silanized microtitre plate.
Figure 5C:
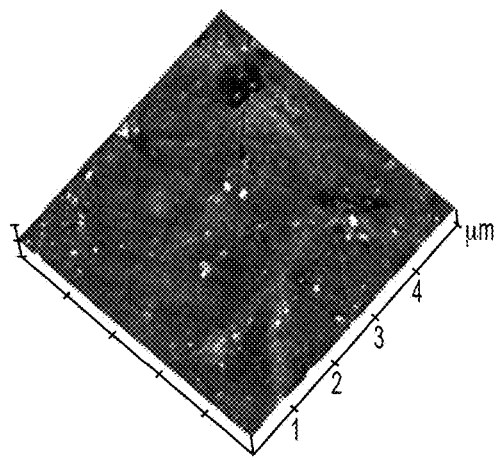
FIG. 5C shows an AFM image of a plasma-treated microtitre plate.
Figure 5D:
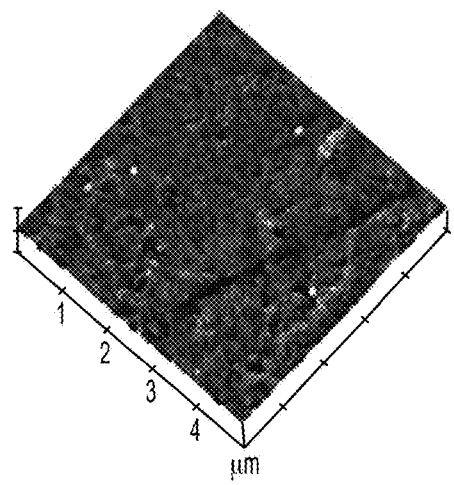
FIG. 5D shows an AFM image of a plasma-treated silanized microtiter plate.

As expected, the untreated polystyrene was hydrophobic (WCA of 95.93±4.57° and showed carbon as the predominant constituent (C1s 92.78±1.43 at. %. FIG. 3 shows the survey spectra of microtitre plates, which indicates the presence of oxygen, and FIG. 4 shows the high resolution C1s spectrum, which indicates the detail the oxygen binding at the surface. Table 1 shows the relative atomic composition in FIG. 3. Table 2 shows the relative concentrations of the species used in the fitting in FIG. 4. After plasma treatment, the polystyrene surface exhibited a significant increase in oxygen concentration (from 5.3 to 16.26 at. %; P<0.005), with trace levels of silicon (<0.5 at. %) detected as well. The high-resolution C1s spectra detailed the plasma-mediated formation of oxygen-based functional groups, including C—O (hydroxyls, ethers) and CdO (epoxy, aldehydes, ketones); the presence of these moieties resulted in an increase in surface hydrophilicity, as confirmed by the 2-fold reduction of the WCA to 48.68±4.37°. The majority of oxygen incorporated into the polymer surface was in the form of singly bonded oxygen; however, C—O was indistinguishable from C—OH in the high-resolution spectra. Gas-phase chemical derivatization analysis (Alexander et al., "Effect of electrolytic oxidation upon the surface chemistry of type A carbon fibres: III. Chemical state, source and location of surface nitrogen" *Carbon*, 34(9), 2093-1102 (2008)) based on fluorine labeling using trifluoroacetic anhydride indicated that nearly all of the C—O/C—OH bonds designated in the high resolution C1s spectra were attributed to C—OH bonds. In contrast to reactive gases, plasmas created in inert gas do not directly introduce functional groups to the surface. However, they do promote surface chemistries via the breaking of bonds, generating reactive sites (dangling bonds) where functional groups can attach (Lock et al., *Plasma Process Polym.*, 6, 234 (2009)); the incorporation of oxygen occurs at those locations upon sample exposure to air after plasma treatment. In this case, hydroxyl groups were most likely formed because of the dissociative adsorption of water upon exposure to ambient air (Petrat et al., *Surf Interface Anal.*, 21, 274 (1994); Petrat et al., *Surf Interface Anal.*, 21, 402 (1994)). As previously noted, the incident ion energy is small in electron beam generated plasmas and thus the creation of reactive sites is not accompanied by significant changes in morphology as shown in FIGS. 5(a) and (c) (P>0.5 data not shown). Thus, incorporation of functional groups, and not surface roughness, is responsible for the observed changes in water contact angle. As will be discussed later, this unique plasma surface treatment promotes uniform silane layer formation and small peptide immobilization.

TABLE 1

| Elements | PS reference (at. %) | Plasma treated PS (at. %) |
|---|---|---|
| C1s | 95.96 | 69.63 |
| O1s | 3.27 | 21.47 |
| Si2p | 0.77 | 3.9 |
| Zn2p | | 1.04 |
| Ca2p | | 1.04 |
| Na1s | | 0.51 |
| Cl2p | | 1.34 |
| F1s | | 1.07 |

TABLE 2

| C1 components | Quantity (at. %) |
|---|---|
| C—C, C—H | 84.65 |
| C—O (C—OH) | 10.67 |
| C=O | 6.03 |
| O—C=O | 1.66 |

A broad range of operating conditions was tested; the various plasma sources and operating conditions are shown in Table 3. Specifically, the pulse width, duty factor, ambient pressure, and total exposure times were varied. However, successful silanization of the polystyrene surface, as determined by attachment of a fluorescently labeled protein, was limited to electron beam produced plasmas and a narrow range of operating conditions (FIG. 2; panels A-B and C-D). The most successful result, determined by the efficiency of covalent biomolecule attachment, were 2 ms pulse widths, 10% duty factor, 90 mTorr operating pressures, and 2 minutes exposure time. It is believed that the relative flux of ions produced under these conditions is important to producing the correct surface conditions within the wells of the microtitre plates.

TABLE 3

| Sample number | Pressure (mTorr) | Gas | Treatment Time (sec) | RF Power (W) | DC Offset (V) | HC Voltage (keV) | Duty (%) | Assay success |
|---|---|---|---|---|---|---|---|---|
| C1-C3 | 90 | Ar | 30 | — | — | 2 | 10 | No |
| C4-C5 | 90 | Ar | 30 | — | — | 2 | 10 | No |
| C6 | 90 | Ar | 60 | — | — | 2 | 10 | No |
| C7 | 90 | Ar | 120 | — | — | 2 | 10 | Yes |
| C10 | 90 | Ar | 300 | — | — | 2 | 10 | No |
| C11 | 60 | Ar | 30 | — | — | 2.4 | 10 | No |
| C14 | 100 | Ar | 120 | — | — | 2 | 10 | No |
| C15 | 110 | Ar | 120 | — | — | 2 | 10 | No |
| C19 | 90 | Ar | 120 | — | — | 2 | 20 | No |
| C20 | 50 | Ar/O$_2$ | 30 | — | — | 2 | 10 | No |
| C21-23 | 90 | Ar | 120 | — | — | 2 | 10 | Yes |

As noted, OH formation occurs after exposure to air. It is likely that similar OH formation could be achieved by treating the plates with plasma produced in reactive backgrounds as well. Candidate gas backgrounds would need to contain some amount of both oxygen and hydrogen such as, but not limited to combinations of O$_2$ and H$_2$, humid air, or H$_2$O or H$_2$O$_2$ vapors in a carrier gas. It is likely that these types of gas backgrounds would also change the operating conditions of the plasma, compared to those described above.

Attempts to use other plasma sources yielded inferior and/or inconsistent results. The reasons for this could be that the range of operating conditions explored was not broad enough to yield a flux of ions comparable to those produced in electron beam plasmas. As noted above, electron beam generated plasmas produce ion fluxes that are characterized by significantly lower kinetic energies. It is known that the energy of ions will depend on the collisionality of the sheaths formed at surfaces and that collisionality will depend on both the plasma density and operating pressure. Thus, one might be able to achieve comparable ion energies in any plasma source.

Characterization of Polystyrene Microtiter Plates after Silanization

XPS, WCA, and AFM measurements were also used to evaluate the efficiency and uniformity of silanization on plasma-treated and untreated polystyrene surfaces. Because a mercaptosilane was used in the silanization step, the presence of sulfur (—SH, binding energy (BE) at 163 eV) and silicon (O—Si—C, BE at 102.6 eV) in the XPS survey spectra served as indicators for silanization. The sulfur and silicon unique to the silane were differentiated from trace element contaminants in the commercial micro-titer plates; sulfur content/contamination from the plates was identified in its oxidized form —SO (BE at 168 eV) and most of the silicon was in the form of Si—O (BE at 103.3 eV) rather than O—Si—C (28).

The XPS results of the silanized, plasma-treated polystyrene surface showed a significant increase in both sulfur and silicon content (≈4.0 at. %) compared to the silanized, untreated polystyrene (<1.3 at. %; P<0.005) Table 4 shows the relative atomic concentrations (%) and standard deviation (values represent means of three determinations±standard deviations) of the measured elements, water contact angles (WCA), and roughness (rms) values of mercaptotosilanized polystyrene microtitre plate before and after argon plasma treatment. These results indicated that the silanization efficiency was enhanced by the plasma-induced modification of the polymer surface. WCA of the plasma-treated silanized plate also indicated that silanization occurred; the WCA value changed from 48.68±4.37° (before silanization) to 60.05±2.08° (after silanization) (P<0.025). The increased WCA value is attributed to the hydrophobic alkyl chain in MPTES and is consistent with literature values (Darian et al., *Biosens. Bioelectronics*, 24, 1744 (2009)). A moderate (but not significant) change in WCA upon silanization was also observed with plates not treated with plasma (P>0.05). However, the final WCA values observed with untreated, silanized plates showed a larger standard deviation, indicating more heterogeneous surface and presumably less efficient silane deposition. The uniformity of silane deposition was further evaluated by atomic force microscopy. Even though the average roughness values of plasma-treated and untreated silanized polymer plates were approximately the same, the standard deviations in both cases were different; a smaller standard deviation was observed after plasma treatment. Furthermore, a significant globular formation on the surface on the untreated plate is also apparent (cf. FIG. 5(*a*) and with FIG. 5(*b*)). Silane aggregation was observed by other research groups as well (Darian et al., *Biosens. Bioelectronics*, 24, 1744 (2009)). It should be noted that after electron beam plasma treatment, only a few aggregates were observed (FIG. 5(*d*)).

TABLE 4

| substrate | MPTES | C | O | Si (102.3 eV) | S (163 eV) | WGE (deg)[a] | rms |
|---|---|---|---|---|---|---|---|
| MT plate | − | 92.8 ± 1.4 | 5.3 ± 1.0 | 1.2 ± 0.6 | 0.3 ± 0.3 | 95.9 ± 4.6 | 7.0 ± 1.7 |
| MT plate | + | 82.7 ± 0.6 | 12.3 ± 1.0 | 0.5 ± 0.1 | 1.3 ± 0.1 | 81.9 ± 10.1 | 8.3 ± 2.4 |
| MT plate, plasma treated | − | 80.9 ± 0.4 | 16.3 ± 0.3 | 0.4 ± 0.1 | ND[b] | 48.7 ± 4.4 | 7.1 ± 1.7 |
| MT plate, plasma treated | + | 72.2 ± 1.1 | 16.5 ± 1.3 | 4.3 ± 0.3 | 4.0 ± 0.3 | 60.1 ± 2.1 | 7.9 ± 0.5 |

[a]Value represents mean ± standard error of four averages at different locations.
[b]ND, not detected.

Biomolecule Immobilization Efficacy

Figure 6:
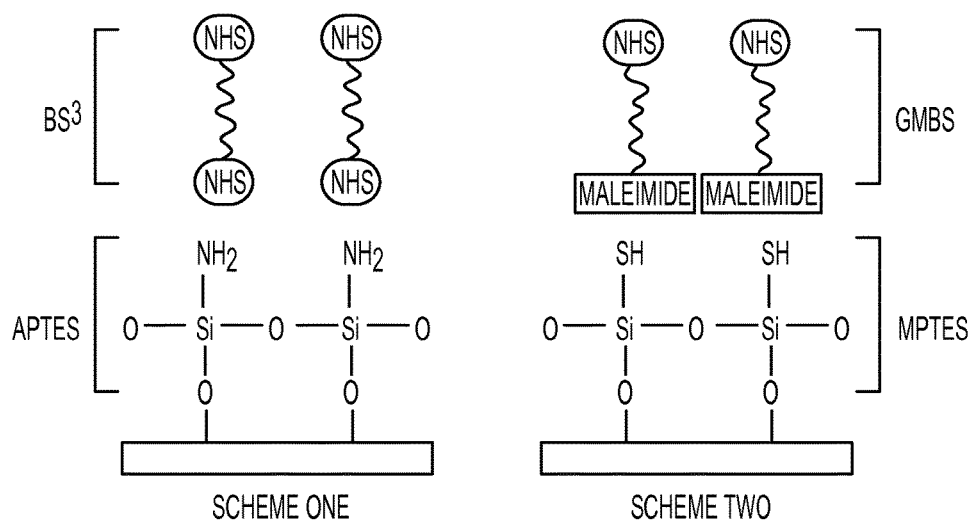
FIG. 6 shows immobilization schemes using aminosilane (left) or mercaptosilane (right).

To demonstrate the suitability of the system for versatile, covalent immobilization of biomolecules to plasma-modified plates, two possible schemes were examined (FIG. 6). In scheme one in FIG. 6, plasma-modified microtiter plates were functionalized with APTES with the intention of presenting surface amine groups. The APTES-treated microwell surfaces were subsequently reacted with an amine-reactive homobifunctional cross-linker (BS[3]), which allows the covalent attachment of Cy3-conjugated IgG. In scheme two in FIG. 6, MPTES was used to form a silane monolayer presenting surface thiol groups. The MPTES-treated microwell surfaces were then reacted with a heterobifunctional cross-linker (GMBS) followed by the covalent attachment of Cy3-conjugated IgG. In both schemes, untreated polystyrene microtiter plates served as controls. On the basis of the two different immobilization schemes presented, BS[3], which contains two amine-reactive NHS groups, is expected to react only with APTES. GMBS, which displays both an NHS group and a maleimide group that react with amine and sulfhydryl groups, respectively, is expected to react with both APTES and MPTES; however, only the MPTES-GMBS combination is expected promote efficient protein conjugation.

As mentioned above, FIG. 2 represents the mean net fluorescence values of attached Cy3-IgG (at 1.0, 3.0, and 10 μg/mL) using immobilization Schemes one and two. To fully demonstrate the ability of the plasma-silane cross-linking methodology to enable multiple immobilization strategies on the same plate, APTES-BS[3], MPTES-GBMS, and combinations thereof (i.e., the "wet" chemistry) were tested on the same plasma-treated 96-well plates, or untreated plates as a control. Fluorescent signals on the plasma-treated plate were shown to be significantly higher than the untreated plate (FIG. 2, compare panels A and C with panels B and D, respectively; P<0.05). Only low fluorescent signals were detected at even the highest protein concentration tested on the untreated plate; these levels, corresponding to <0.02 pmol/well, are presumably due to background levels of adsorption onto the microtiter plate surface, and are well-below published saturation values for IgG adsorbed to polystyrene (0.35-0.5 pmol/cm[2] (Rossier et al., "*Langmuir,* 16, 8489 (2000); Salonen et al., *Immunol. Methods,* 30, 209 (1979); Nygren et al., *Immunol. Methods,* 101, 63 (1987)). Although some immobilization was observed when GMBS was used to cross-link the antibody to APTES-treated plates. Cy3-IgG immobilization on APTES-coated surfaces was much more efficient when BS[3] was used (FIG. 2, panel A);

GMBS-mediated linking of Cy3-IgG to APTES surfaces may have occurred by reaction with free thiols present on native or partially denatured IgGs, or potentially from low levels of maleimide reaction with excess amines on IgG surfaces (Brewer et al., *Anal. Biochem.*, 18, 248 (1967)). On the other hand, bioimmobilization on MPTES coated surfaces was greatest in the presence of GMBS cross-linker (FIG. 2, panel C). Although the MPTES-BS[3] demonstrated higher relative fluorescence, it was comparable to the control samples containing no cross-linker.

Figure 7:
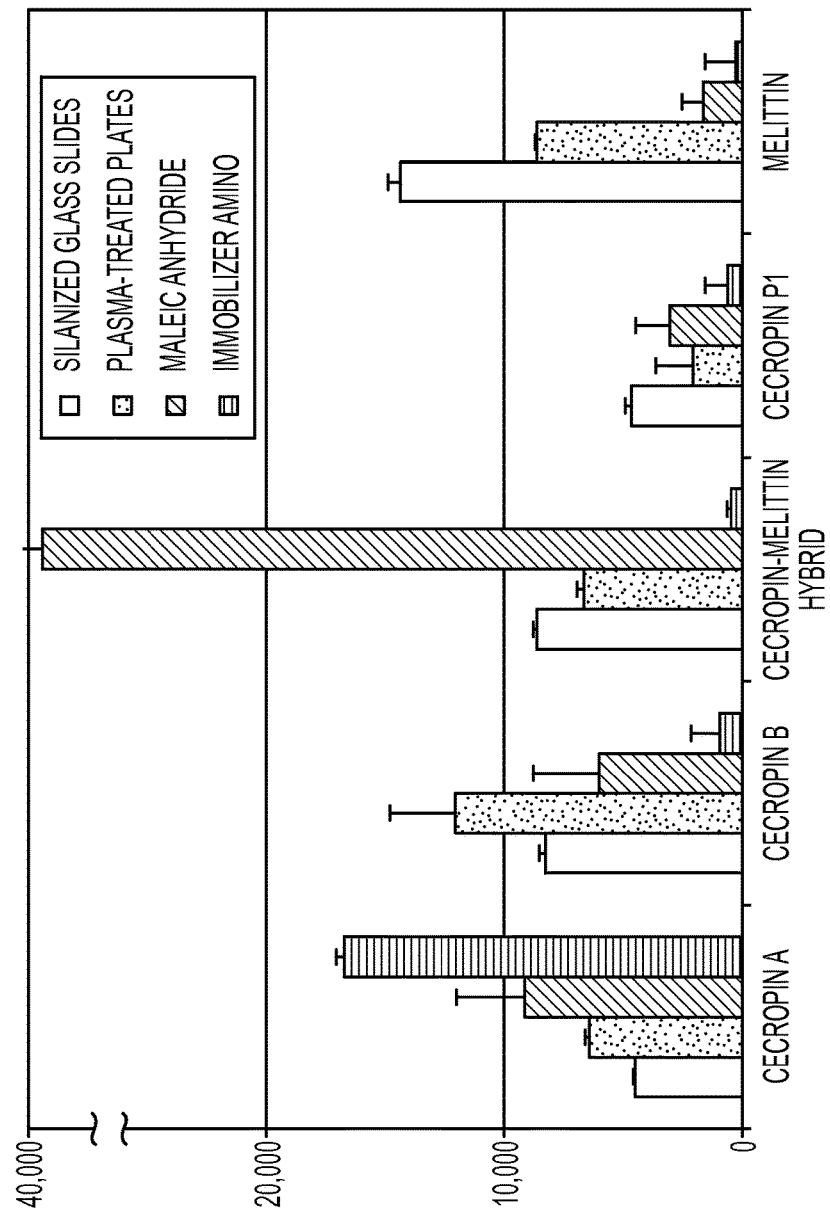
FIG. 7 shows binding of Cy3-LPS by antimicrobial peptides (cecropin A, melittin, cecropin A-melittin hybrid, and cecropin P1) immobilized onto silanized glass slides (white bars), plasma-modified microtiter plates (via MPTES and GMBS, gray bars), and commercial amine-directed, preactivated plates (striped bars). As two instruments were used to obtain and extract fluorescence data (microtiter plate reader, confocal microarray scanner), all values were normalized to those obtained with melittin.

IgGs and many other large biomolecules can be immobilized using a wide range of substrates and linking procedures with minimal impact on binding activity. However, smaller biomolecules such as peptides, saccharides, and small proteins are highly sensitive to surface morphology and orientation when immobilized (Ngundi et al., *Sens. Lett.*, 5, 621 (2007); Inamori et al., *Anal. Chem.*, 80, 643 (2008); Disney et al., *Chem. Biol.*, 11, 1701 (2004); Kulagina et al., *Anal. Chim. Acta*, 575, 9 (2006); Kulagina et al., *Anal. Chem.*, 77, 6504 (2005)). To demonstrate that the described chemistry could be applied to this latter category of biomolecules, a series of naturally occurring antimicrobial peptides were utilized as model ligand-binding molecules. These biomolecules are capable of binding to a large variety of microbial cells with different affinities, which makes them useful in detection assays (Kulagina et al., *Anal. Chem.*, 77, 6504 (2005)); the ability to distinguish between different categories of microbial cells based on their patterns of binding to different peptides can be used for rapid and broad-spectrum screening (Kulagina et al., *Sens. Actuators B*, 121, 150 (2007); Kulagina et al., *Anal. Chim. Acta*, 575, 9 (2006); Taitt et al., in *Peptide Microarrays: Methods and Protocols*; Cretich, M. Chiari, M., Eds.; Springer: New York, 2009; p 233). Previous studies have shown that when immobilized onto glass slides using an amine-directed immobilization strategy (MPTES treatment, followed by GMBS, analogous to scheme two), the peptides displayed unique patterns of binding to Gram-positive and -negative bacteria (Shriver-Lake et al., In *Biosensors and Biodetection: Methods and Protocols: Electrochemical and Mechanical Detectors, Lateral Flow and Ligands for Biosensors*; Rassoly, A., Herold, K. E., Eds.; Springer: New York, 2008; p 419, North et al., *Anal. Chem.*, 82, 406 (2009)) and to the Gram-negative biomarker lipopolysaccharide, LPS (FIG. 7, white bars). Surprisingly, we observed very different patterns of LPS binding when utilizing commercial, preactivated microtiter plates (Immobilizer amino, maleic anhydride; FIG. 7, striped bars). Although both types of commercial plates use amine-directed chemistry (as did the glass slides), the differences in reactive groups, overall surface characteristics, and linker lengths appear to affect the immobilized peptides' ability to bind the target LPS, presumably by altering peptide orientation, density, freedom of movement, and/or the number and identity of linked amino acid side chains. However, when plasma-treated plates were processed using analogous chemistry as used on the glass slides (plasma-treatment→silanization with MPTES→cross-linking with GMBS), the binding pattern observed (FIG. 7, gray bars) was similar to that of the gold standard glass slides. The ability to transition an immobilization methodology directly from one platform (silanized glass slides) to another (plasma-treated, silanized plates), with minimal alteration of binding specificity, illustrates a potential advantage conferred by the method described here.

Comparison Between Plasma-Treated and Commercial Microtiter Plates

Figure 8:
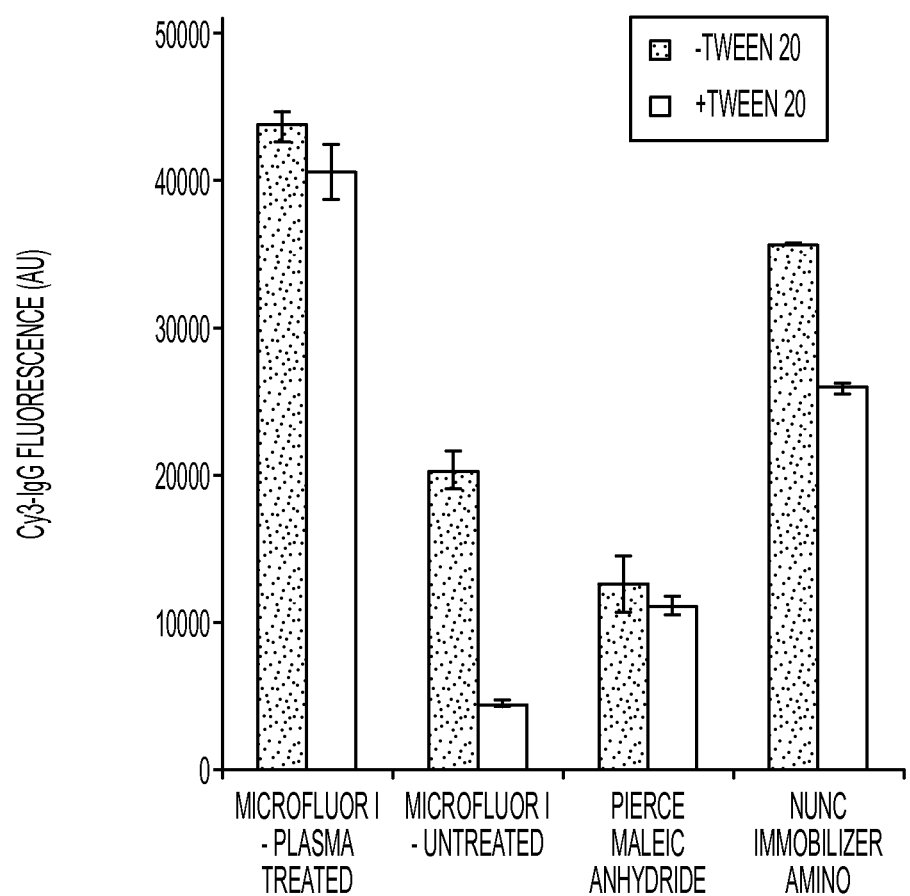
FIG. 8 shows fluorescent intensities of Cy3-IgG (10 µg/mL) immobilization to plasma-treated Microfluor I (covalent immobilization following Scheme Two), Microfluor I (physisorption), Pierce Reactibind Maleic Anhydride, and NUNC Immobilizer Amino (covalent immobilization according to manufacturers' instructions); gray bars=no detergent wash, white bars=detergent wash.

The issues of biomolecule denaturation, desorption, and/or loss of biomolecule activity that could occur when biomolecules are immobilized through physisorption have been recognized and not, surprisingly a number of commercial microtiter plate are available in preactivated form for covalent attachment of biomolecules (amine-directed immobilization: Immobilizer Amino and maleic anhydride-functionalized; sulfhydryldirected immobilization: maleimide-functionalized). The efficacy of biomolecule immobilization (using immobilization scheme two) on plasma-treated, silanized plates was compared with those of commercial microtiter plates utilizing both physisorption and amine-directed, covalent attachment strategies. Protein immobilization efficiency (fluorescence of immobilized Cy3-IgG) was determined for each kind of plate before and after a stringent detergent wash (buffer with 0.5% Tween-20; FIG. 8). Consistent with data presented in FIG. 2, plasma-treated plates exhibited significantly higher fluorescent signal than untreated plates (≈2-fold increase) where immobilization has occurred via physisorption ("Microfluor I Untreated"; $P<0.005$). As expected, the difference between the plasma-treated and untreated plates increases dramatically (≈8-fold difference) after a detergent wash. Although covalent attachment of IgG to the commercial preactivated plates (Maleic anhydride, NUNC Immobilizer Amino) preserved a greater proportion of the attached biomolecules, the overall binding efficiency of plasma-/silane-treated plates was still superior ($P<0.01$).

Example 2

The microtitre plates were placed on a 10.2 cm diameter stage located at 2.5 cm from the nominal edge of the electron beam. The stage was held at ground potential and room temperature. The total gas flow rate was held constant at 50 sccm. The experimental conditions are summarized in Table 5.

TABLE 5

| Exp. # | Pressure (mTorr) | Time (min) | Duty factor (%) |
| --- | --- | --- | --- |
| 1 | 60 | 0.5 | 10 |
| 2 | 90 | 2 | 10 |
| 3 | 95 | 2 | 10 |
| 4 | 90 | 1 | 10 |
| 5 | 90 | 5 | 10 |
| 6 | 90 | 2 | 20 |

As variation in pressure has the greatest influence on the production of plasma species—charged particles, metastables and photons, it is expected to produce the most pronounced difference in oxygen incorporation. The highest degree of oxygen incorporation was observed at a pressure of 90 mTorr (exp #2, Tables 5, 6) (O/C=0.3) resulting in the highest polar component of the surface energy as well. The most likely mechanism of polystyrene modification in argon is the formation of carbon-centered polymer free radicals (P•), which preferentially crosslink. However, chain scission and formation of polyenes are also possible (Knobloch, *Angew. Makromol. Chem.*, 176-177, 333 (1990)). Higher pressures (exp #3, Table 5) did not improve the surface chemical composition. In fact, the O/C ratio, C—O group concentration and $\gamma_p$ decreased. This might be due to an excessive ion flux, which may cause an increase in etching and favor chain scission over crosslinking as the dominant mechanism. The surface roughness decreased at all pressures, which might be caused by ablation of low molecular weight fragments residing on the polymer surface.

TABLE 6

| Exp # | O/C | C—C(H)[a], C—CO$_2$[a] | C—O[a] | C=O[a] | COO[a] | π-π*[a] | $\gamma_p^b$ | $\gamma_d^b$ | $\gamma_{tot}^b$ | RMS[c] | bioefficiency |
|---|---|---|---|---|---|---|---|---|---|---|---|
| Ref | 0.03 | 92.61 | 1.58 | 0 | 0 | 5.81 | 0 | 40 | 40 | 19 | – |
| 1 | 0.27 | 89.84 | 5.12 | 2.94 | 1.08 | 1.01 | 24 | 32 | 56 | 11 | – |
| 2 | 0.30 | 86.07 | 8.24 | 4.04 | 1.65 | 0 | 26 | 38 | 64 | 12 | + |
| 3 | 0.20 | 73.03 | 5.56 | 3.24 | 1.05 | 0 | 10 | 43 | 53 | 12 | – |
| 4 | 0.22 | 77.74 | 3.14 | 0.33 | 0 | 0.9 | 20 | 36 | 56 | 11 | – |
| 5 | 0.23 | 87.53 | 7.8 | 2.85 | 1.02 | 0.8 | 19 | 39 | 58 | 16 | – |
| 6 | 0.14 | 81.32 | 6.17 | 1.56 | 0 | 0 | 13 | 40 | 53 | ND[d] | – |

[a]Concentration of functional groups was measured in at. %.
[b]Surface energy was measured in mJ/m$^2$.
[c]RMS roughness was measured in nanometers (nm).
[d]ND means not determined.

Variations in both treatment time and duty factor at a fixed pressure led to similar conclusions. Increase in treatment time from 1 to 2 minutes (exps #4 and 2, Tables 5, 6) resulted in higher O/C ratios, increased amount of oxygen functionalities (C—O, C=O, COO groups) and improved polar component of the surface energy with no change in surface roughness. However, when the polystyrene substrate was treated for 5 minutes (exp #5, Tables 5, 6) the O/C ratio decreased and surface roughness increased. These results suggested that prolonged plasma exposure increases etching, increases surface roughness, and promotes chain scission and not crosslinking. Increase in duty factor (exp #2 and #6) did not increase the oxygen incorporation. In fact, it resulted in decrease of O/C ratio as well as a decrease of the polar component of the surface energy by a factor of two. Although the reasons are not clear, it appears that reducing the time between pulses does not promote the incorporation of OH-groups.

Figure 9:
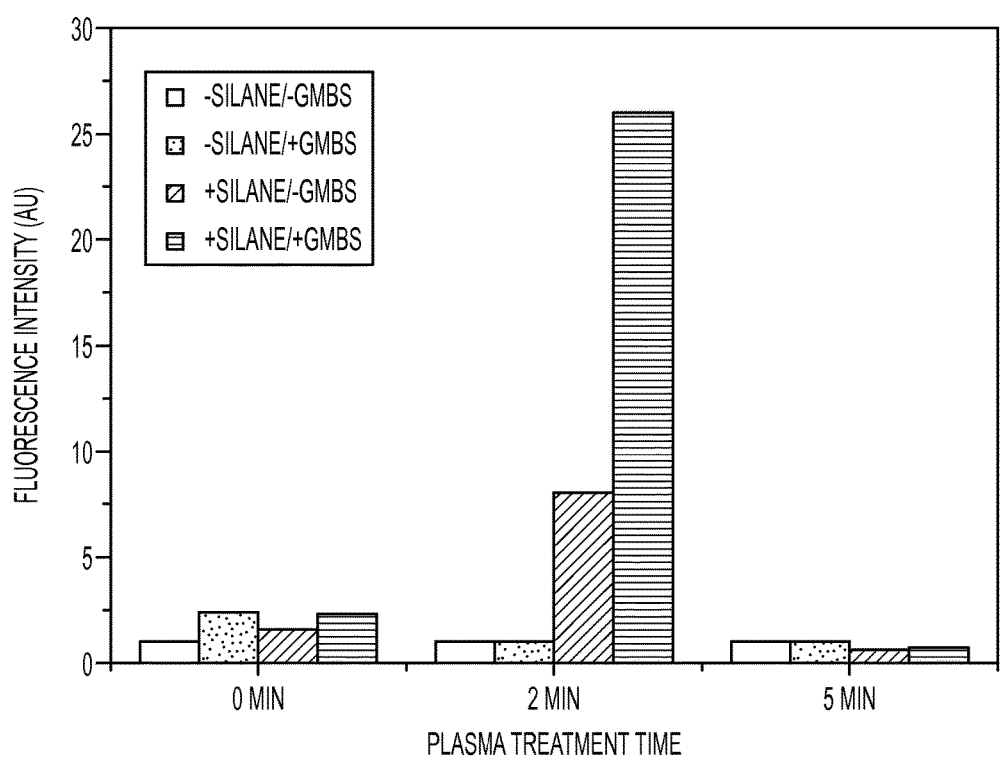
FIG. 9 shows biomolecule immobilization efficacy as a function of plasma treatment time.

Covalent bioimmobilization was observed only at a pressure of 90 mTorr, treatment time of 2 minutes and 10% duty factor (exp. #2 Table 6, FIG. 9). At this condition the increase in fluorescent signal, signifying specific biomolecule attachment, was 26-fold above the background levels. These results are in direct correlation to the presence of oxygen functional groups on the polystyrene surface. That is, when the oxygen functionalities concentration on the polymer surface was optimized, it allowed for efficient silanization and thus specific biomolecule immobilization occurs.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
   treating an organic polymer microtitre plate with an electron beam-generated plasma;
   exposing the treated plate to air or an oxygen- and hydrogen-containing gas;
   wherein the treating and exposing generates hydroxyl groups on the surface of the plate.

2. The method of claim 1;
   wherein the plasma is generated in argon;
   wherein the argon gas pressure is 90 mTorr+/10%;
   wherein the treatment time is 2 min+/10%;
   wherein the electron beam is pulsed at 50 Hz+/−10%; and
   wherein the electron beam is operated with pulse width of 2 ms+/−10%.

* * * * *